United States Patent [19]

Diamond

[11] Patent Number: 5,662,888
[45] Date of Patent: Sep. 2, 1997

[54] TOOTHPASTE FOR SMOKERS FOR SOLUBILIZING AND REMOVING TOBACCO TARS

[75] Inventor: Jeffrey H. Diamond, Palm Beach, Fla.

[73] Assignee: Jeffrey Mitchell Laboratories, Lake Worth, Fla.

[21] Appl. No.: 642,358

[22] Filed: May 3, 1996

Related U.S. Application Data

[62] Division of Ser. No. 453,353, May 30, 1995, Pat. No. 5,514,366, which is a continuation of Ser. No. 291,054, Aug. 15, 1994, abandoned, which is a continuation of Ser. No. 043,891, Apr. 7, 1993, abandoned.

[51] Int. Cl.$^6$ .................. A61K 7/16; C11D 7/50
[52] U.S. Cl. .................. 424/49; 134/2; 252/364; 510/116
[58] Field of Search .................. 424/49–58

[56] References Cited

U.S. PATENT DOCUMENTS

| | | |
|---|---|---|
| Re. 32,771 | 10/1988 | Eoga .................. 252/99 |
| 1,526,940 | 2/1925 | Staegemann . |
| 2,124,971 | 7/1938 | Eisenberg et al. . |
| 2,519,665 | 8/1950 | Kilppert . |
| 2,744,049 | 5/1956 | Salzmann et al. . |
| 2,921,886 | 1/1960 | Panepinto . |
| 3,137,632 | 6/1964 | Schuraldi . |
| 3,164,524 | 1/1965 | Fand et al. . |
| 3,497,590 | 2/1970 | Eigen . |
| 3,553,314 | 1/1971 | Francis . |
| 3,553,315 | 1/1971 | Francis . |
| 3,652,420 | 3/1972 | Hill .................. 252/101 |
| 3,664,613 | 5/1972 | Moeller et al. . |
| 3,737,522 | 6/1973 | Francis . |
| 3,839,213 | 10/1974 | Hill .................. 252/89 |
| 3,840,657 | 10/1974 | Norfleet . |
| 3,899,437 | 8/1975 | Regan et al. .................. 252/106 |
| 3,935,304 | 1/1976 | Januszewski et al. . |
| 3,935,305 | 1/1976 | Delaney et al. . |
| 3,937,804 | 2/1976 | Delaney et al. . |
| 3,947,570 | 3/1976 | Pensak et al. .................. 424/54 |
| 3,966,901 | 6/1976 | Cullum et al. . |
| 3,988,434 | 10/1976 | Schole et al. .................. 424/54 |
| 3,992,519 | 11/1976 | Hofmann et al. . |
| 4,115,293 | 9/1978 | Schoenholz et al. .................. 252/152 |
| 4,130,636 | 12/1978 | Tomlinson . |
| 4,150,151 | 4/1979 | Pader et al. .................. 424/56 |
| 4,155,868 | 5/1979 | Kaplan et al. .................. 252/95 |
| 4,206,198 | 6/1980 | Schmolka . |
| 4,223,003 | 9/1980 | Scheller . |
| 4,303,648 | 12/1981 | Witzel et al. .................. 424/158 |
| 4,323,552 | 4/1982 | Schmolka . |
| 4,383,987 | 5/1983 | Kiozpeoplou . |
| 4,393,042 | 7/1983 | Battista . |
| 4,409,202 | 10/1983 | Witzell et al. .................. 424/49 |
| 4,420,471 | 12/1983 | Elton et al. .................. 424/49 |
| 4,428,929 | 1/1984 | Wicheta et al. .................. 424/49 |
| 4,431,631 | 2/1984 | Clipper et al. .................. 424/53 |
| 4,511,486 | 4/1985 | Shah .................. 252/90 |
| 4,518,520 | 5/1985 | Eoga .................. 252/114.13 |
| 4,522,806 | 6/1985 | Muhlemann et al. .................. 424/52 |
| 4,537,778 | 8/1985 | Clipper et al. . |
| 4,540,504 | 9/1985 | Eoga .................. 252/99 |
| 4,550,018 | 10/1985 | Ambike et al. .................. 424/52 |
| 4,610,872 | 9/1986 | Lynch .................. 424/49 |
| 4,657,758 | 4/1987 | Goldemberg et al. . |
| 4,666,708 | 5/1987 | Goldemberg et al. .................. 424/49 |
| 4,684,317 | 8/1987 | Clipper et al. .................. 424/52 |
| 4,701,223 | 10/1987 | Eoga .................. 151/2 |
| 4,747,417 | 5/1988 | Beskin .................. 131/270 |
| 4,807,679 | 2/1989 | Eoga .................. 151/2 |
| 4,992,259 | 2/1991 | Schiraldi et al. .................. 424/49 |
| 5,032,385 | 7/1991 | Reed et al. . |
| 5,130,122 | 7/1992 | Tabibi et al. .................. 424/49 |
| 5,145,664 | 9/1992 | Thompson .................. 424/49 |
| 5,178,869 | 1/1993 | Ebine et al. .................. 424/101 |

*Primary Examiner*—Shep Rose
*Attorney, Agent, or Firm*—Pollock, Vande Sande & Priddy

[57] ABSTRACT

A toothpaste for smokers for solubilizing and removing cigarette tar deposits on the teeth, gums, tongue, other surfaces of the oral cavity, and dentures of smokers including at least one nonionic surfactant in a concentration range of from about 0.3% to about 6.5% by weight, methyl salicylate in a tobacco tar solubilizing concentration range of from about 0.06% to about 0.20% by weight, at least one essential oil in a concentration range of from about 0.30% to about 2.0% by weight, ethyl alcohol in a concentration range of from about 12.0% to about 20.0% by weight, at least one anionic surfactant in a concentration range of from about 0.3% to about 4.5% by weight, and a gelling agent.

21 Claims, No Drawings

TOOTHPASTE FOR SMOKERS FOR SOLUBILIZING AND REMOVING TOBACCO TARS

This application is a Divisional of U.S. patent application Ser. No. 08/453,353, filed May 30, 1995, now U.S. Pat. No. 5,514,366, which is a Continuation of U.S. patent application Ser. No. 08/291,054, filed Aug. 15, 1994 which is a Continuation of U.S. patent application Ser. No. 08/043,891, filed Apr. 7, 1993, both now abandoned.

FIELD OF THE INVENTION

The invention relates to dental and oral hygiene, and in particular, to a preparation to dissolve and/or disperse and remove deposits on the teeth, gums, tongue, and other surfaces in the oral cavity.

BACKGROUND OF THE INVENTION

It is well known that tobacco smoking can cause the deposition of materials on the teeth, tongue, gums, and other surfaces in the oral cavity of smokers. The result of the deposition of these materials is well known by any one who smokes or knows someone who smokes. The most well known of these effects include the discoloration of the teeth and other surfaces within the oral cavity such as the gums and tongue and the causing of bad breath. Stained teeth can be unsightly and bad breath can be unpleasant for the smoker and those he or she comes into contact with. Additionally, as described below, the materials deposited on the interior surface of the mouths of smokers can lead to health problems, such as tooth decay and gum disease. It is also well known that food and oils and other materials contained in the food can be deposited on the surfaces of peoples' mouths.

The major constituent of deposits caused by smoking is commonly known as "tar". Tobacco tar is loosely defined as a dark, oily, viscid blend of polycyclic aromatic and aliphatic hydrocarbons, although tar also contains other compounds. Tar is produced as tobacco in a cigarette, cigar, or pipe burns. The tar is contained within the smoke produced by the burning of the tobacco.

As a smoker smokes a cigarette, pipe, or cigar, he or she inhales the tar along with the other tobacco combustion products as the smoke is sucked into the mouth and eventually into the lungs. The smoke is then blown out of the body as the smoker exhales and the smoke passes through the mouth of the smoker once again. Therefore, the smoke passes through the mouth of the smoker twice, upon inhalation and exhalation, providing ample opportunity for the compounds in the tar to come into contact with the teeth, gums, tongue, and other surfaces in the oral cavity and be deposited thereon. Obviously, the more a person smokes, the more tar will be deposited in the mouth of the smoker.

Dentists and hygienists can immediately detect smokers by the heavy staining of the lingual surface of the mandibular anterior teeth. These stains are observed as being resinous in nature. According to a recent study by the Centers for Disease Control, smokers' teeth are generally twice as stained as non-smokers'. McKendrick, Barbenel, and McHugh, Indiana School of Dentistry (1970).

Due to the hydrophobic nature of the compounds contained within the tar, the tar is not easily dissolved or dispersed by commonly available over the counter mouth treatments such as toothpastes, gels, and oral rinses. As a result, tar can build up on the teeth, dentures, denture plates, artificial teeth and other surfaces of the smoker's mouth causing, among other things, staining of plaque and calculus and an aesthetically displeasing appearance of the smoker's teeth and mouth. Additionally, since the compounds in tar have an unpleasant aroma, their deposition and residence within the mouth of smokers can cause chronic halitosis. The difficulty in removing the tar deposits within the mouth of smokers is increased by there viscid nature. Many compounds contained within food and other substances that come into contact with peoples' mouths have a chemical nature similar to that of tobacco tar and can also be deposited on the surfaces of the mouth, build up there, and cause problems similar to those caused by the tobacco tar.

Therefore, as the tar deposits as well as deposits of other materials, such as oils in food, build up in the mouth of the smokers, not only are the teeth and the rest of the mouth discolored by the tar and the breath of the smokers caused to take on a malodorous nature, the tar can become incorporated into the plaque and calculus which forms on the teeth. Because of its especially tenacious nature, the calculus is only removable by a dentist or dental hygienist with a steel pick. Because the tar can reduce the immune response, bacteria has the opportunity to proliferate. Bacterial can cause tooth decay, gingivitis, bleeding and swelling of the gums, and periodontal disease. Therefore, tobacco tar is a real health problem.

As discussed above, tar is especially difficult to remove once deposited on the surface of the teeth, gums, tongue, and the rest of the oral cavity. Materials in food and other substances coming into contact with peoples' mouths can also be just as difficult to remove. In an attempt to remove tar and other deposits from teeth, products such as toothpastes and gels were developed which claim to remove tobacco tar. Known tar removing products remove the tar by physical abrasion, similar to how sandpaper removes the surface layer of wood, for example. These products usually include an aluminum or silicon based abrading material to physically remove the tar from the surfaces in the mouth. All known anti-tobacco stain products on the market are in toothpaste form. Since these known products do not include ingredients which dissolve and/or disperse tar, but rather, remove tar by physical abrading action, they rub the tar off the surfaces of the mouth as the smoker brushes his or her teeth.

Unfortunately, the abrading materials in these known oral preparations do not differentiate between tar and other materials, such as the actual surface of the teeth. Therefore, in addition to removing tobacco tar, these materials can actually remove enamel from the teeth themselves. Removal of the enamel could cause the teeth to become sensitive, which can cause individuals to avoid brushing their teeth, which may lead to tooth loss. For example, the outer enamel layer can be partially removed by these known products, thereby damaging the teeth and creating scratches on the surface of the teeth.

These scratches can make the teeth more susceptible to decay and endanger the softer interior layers of the teeth. Also, the scratches can act to increase the surface area of the teeth, thereby increasing the number of places where bacteria can attach to the surface of the tooth and potentially cause tooth decay. These abrasive cleaners are also not capable of removing tar from microscopic concavities in the teeth which are too small for the abrasives to enter or from any surface which the abrasive materials can not be rubbed against, such as the interproximal spaces between teeth and some gingival spaces between the teeth and gums.

Therefore, these known abrasive materials which claim to remove tobacco tar from the surfaces of teeth can in fact leave much tar untouched on teeth and oral soft tissue and actually cause damage to the oral cavity. For these reasons, dentists usually do not recommend the use of these types of oral preparations.

As opposed to abrading compositions, it would be desirable to have an oral rinse mouthwash that could remove tar from all surfaces in the mouth of a smoker and not physically harm the tooth surface. It would be advantageous to have a mouthwash that could dissolve and/or disperse the tobacco tar thereby removing it from the mouth without any of the adverse effects described above. However, no known available oral rinse product available on the market today is directed to or is capable of preforming the function of dissolving or dispersing tobacco tar effectively.

SUMMARY OF THE INVENTION

The present invention provides an oral rinse composition which includes a unique combination and concentration of nonionic surfactants and cyclic aromatic essential oils. Both the combination and amounts of these ingredients is unknown in the prior art. The oral preparation includes at least one nonionic surfactant with a concentration range from about 0.3% to about 6.5% by weight. Additionally, at least one cyclic, preferably aromatic, essential oil in a concentration range of from about 0.03% to about 3.5% by weight is included in the oral preparation of the present invention.

The present invention is also directed to a method of removing deposits on the teeth, dentures, dental plates, gums, tongue, and other surfaces of the oral cavity. The method includes introducing into the mouth a preparation for dissolving or dispersing the deposits. The preparation includes at least one nonionic surfactant having a concentration range from about 0.3% to about 6.5% by weight is also included. Additionally, at least one cyclic aromatic essential oil in a concentration range of from about 0.03% to about 3.5% by weight is included in the oral preparation of the present invention.

The composition and method of the present invention produce the unexpected results of being able to remove tar without abrasive action or physically damaging teeth unknown in the prior art.

DETAILED DESCRIPTION OF THE PREFERRED EMBODIMENTS

The active ingredients of the oral preparation of the present invention for removing deposits on the teeth, gums, tongue, and other surfaces in the oral cavity preferably include at least one nonionic surfactant and at least one cyclic, preferably aromatic, essential oil. Preferably, the present invention may also include at least one anionic surfactant, although the present invention will still function well without an anionic surfactant component. Additionally, the preparation of the present invention may also include flavorings, solvents, a vehicle for the preparation, humectants, and preservatives.

It has been found that including the ingredients in the combination in the present invention and the amounts of the present invention provides the preparation of the present invention with the ability to dissolve and/or disperse material deposited on the surface of the teeth, gums, tongue, and other surfaces of the oral cavity. Specifically, the present invention has the ability to dissolve and/or disperse tobacco tar on contact. Such an ability to dissolve and/or disperse tar is unknown among known oral preparations. The preparation of the present invention may be included in an oral rinse or in toothpastes or gels, or powders, or in any other effective form, simply with the addition to the above ingredients of a thickening or gelling agent.

The nonionic surfactant component of the present invention may act as a tar solubilizer and/or flavor solubilizer, among other things. Any pharmaceutically or orally acceptable nonionic surfactant may be used according to the present invention. Examples of nonionic surfactants which maybe used in the present invention include glycerol-polyethylene glycol oxystearate (PEG 40, Cremophor RH40 and 60 available from BASF), polyoxyethylene esters or sorbitol laurate esters, such as polyoxyethylene sorbitan monolaurate, polyoxyethylene sorbitan monoisostearate, polyoxyethylene sorbitan monostearate, polyoxyethylene sorbitan monooleate, polyoxyethylene or sorbitol laurate esters including polysorbates, and block polymers of polyoxyethylene and polyoxypropylene (pluronic 127). Preferably, the concentration range of nonionic surfactants included in the present invention is from about 0.3% to about 6.5% by weight.

The present invention may also include at least one anionic surfactant. The anionic surfactant component of the present invention may act as a sudsing agent and tar co-solubilizer, among other things. Any pharmaceutically or orally acceptable anionic surfactant may be used according to the present invention. Examples of anionic surfactants which may be used in the present invention include sodium lauryl sulfate and a pharmaceutical or oral grade of sodium ether lauryl sulfate. Preferably, the concentration range of anionic surfactants included in the present invention is from about 0.3% to about 4.5% by weight.

In contrast to the prior art in which anionic surfactants are included in dental rinses to create mild sudsing and to help remove some oral debris such as food and related oils, the present invention may include anionic surfactants in concentration ranges high enough in conjunction with other ingredients to actually dissolve and/or disperse the tobacco tar. In addition, the nonionic surfactants are used in the prior art only to keep the essential oils used as flavors in solution. Again, in the present invention, the nonionic surfactants are included to help solubilize the tar they come in contact with and are present in such high concentration ranges that they preform this function.

Tobacco tar contains much higher molecular weight materials than the standard essential oils used as flavors. Therefore, to solubilize tar, the amount of nonionic surfactants or the amount of the combination of nonionic and anionic surfactants, if anionic surfactants are included in the formulation, as a percentage of total weight is much greater in the present invention than in the prior art. It is the high concentration and combination of surfactants in the present invention which in part provides it with its superior and unexpected ability to dissolve and/or disperse tobacco tar as compared to the prior art. Most prior art mouthwashes contain from about 0.02% to about 2.0% by weight surfactants. On the other hand, the present invention includes surfactants in a concentration range of from about 0.3% to about 11.0% by weight.

The present invention also preferably includes a different surfactant blend than prior art mouthwashes. The only oils that prior art mouthwashes are designed to solubilize are the flavors and essential oils, not the oils included in tobacco tar and other oily substances deposited in the mouth. Preferably, the present invention includes a combination of anionic and nonionic surfactants, including at least one of each.

The active ingredients of the present invention also include aromatic essential oils such as methyl salicylate. The aromatic essential oil component of the present invention may act as a tar solubilizer, among other things. Any pharmaceutically or orally acceptable aromatic essential oil may be used according to the present invention. Examples of aromatic essential oils which may be used in the present invention include methyl salicylate, anise, anethol, bergamot, camphor, cinnaminic anhydrides, clove, eucalyptol, peppermint, spearmint, and thyme, among others. Preferably, the concentration range of aromatic essential oils included in the present invention is from about 0.03% to about 3.75% by weight.

In the prior art, essential oils are used mainly as flavors and are typically used in a concentration range of from only about 0.05% to about 0.30% by weight for flavoring, and do not have any other function. In fact, they are not present in high enough concentrations to be effective in any other manner, except for a slight anti-microbial effect. These aromatic essential oils in combination with the anionic and nonionic surfactants also present in higher concentrations than are known in the prior art help to dissolve and/or disperse significantly more tar than known prior art dental preparations. A significant difference between the present invention and the prior art is that in the prior art methyl salicylate is included mainly as a flavoring; in the present invention methyl salicylate when included in the relatively high concentration ranges will act to solubilize tobacco tar, in conjunction with other ingredients.

Other ingredients included in the present invention include a vehicle for the oral preparation, solvents, humectants, sweeteners, flavors, and preservatives. The preferred vehicle for an oral rinse prepared according to the present invention is water. With water used as the vehicle to prepare such a rinse, the water is present in the concentration range of from about 50 to about 85% by weight. Additional vehicles which may be included in the present invention include pastes and gels, which allow the present invention preparation to be used as a tooth paste rather than a rinse.

The present invention may also include a solvent in a concentration range of from about 3.0% to about 30.0% by weight. Solvents help to keep all of the ingredients in the dental preparation dissolved. The solvents which may be included in the present invention include ethanol. However, any pharmaceutically or orally acceptable solvent may be used.

Humectants may also included in the present invention in concentration ranges of from about 3% to about 15% by weight. Humectants help to stabilize the water content of the solution. Humectants which may be used in the present invention include, among others, glycerine and sorbitol. However, any pharmaceutically or orally acceptable humectant may be used in the preparations of the present invention. The humectant also helps to give the rinse a better feel to the mouth.

The present invention may also include essential oils as flavoring components in addition to the methyl salicylate discussed above as a tar solubilizer. Any of the cyclic, aromatic essential oils which may be used to solubilize tar may also be used as flavoring.

Additionally, the present invention may include a preservative in concentration ranges of from about 0.05% to about 2.0% by weight. Such preservatives include benzoic acid and sodium benzoate, among others, however, any pharmaceutically or orally acceptable preservative may be used to prepare the present invention.

Further, the present invention may include a sweetener, such as sodium saccharin, in a concentration range of from about 0.01% to about 0.7% by weight. A color may also be added to the preparation of the present invention in a concentration range of from about 0.001% to about 0.5% by weight.

By including the plurality of different surfactants and the methyl salicylate, the present invention achieves it superior ability to remove tar from surfaces within the mouths of smokers. The different surfactants have different functionalities which act on the tar in different manners. For instance, the nonionic surfactants are tar solubilizers and the anionic surfactants are detergents and detergent builders/sudsing aids. The anionic surfactants help to suspend the dissolved or dispersed tar particles as they are removed from the surfaces of the mouth. The anionic surfactants include hydrophobic hydrocarbon side chains which help to solubilize the alkyl portions of the tar. In addition, the methyl salicylate helps to solubilize the molecules in the tar which include cyclic members. No known prior art dental preparation includes the combination and amount of ingredients included in the present invention. It is the composition of the present invention which provides it with the unexpected ability to dissolve and/or disperse tar as effectively as it does in the amounts that it does.

In addition to the oral rinse form of the product, the preparation of the present invention may be included in gels or pastes utilizing thickening or gelling agents. Such agents include, among others, silica aerogels, pyrogenic silica, silica precipitates, carboxymethyl cellulose, carboxyvinyl polymers, xanthan gum, and carrageenan.

The following examples are of preferred embodiments are only illustrative. All amounts and proportions referred to here and in the claims are by weight unless otherwise indicated. N/A indicates that the ingredient is not included in that example solution. The preparations of the examples are all included in an oral rinse. However, these same compositions could be modified to be included in a toothpaste or gel for example, by including a thickening and/or gelling agents.

TABLE 1

| Ingredient | Example 1 | Example 2 | Example 3 |
| --- | --- | --- | --- |
| Solvent Alcohol | | | |
| Ethanol | 16.5 | 15.0 | 12.5 |
| Vehicle | | | |
| Water | 66.5 | 68.40 | 77.90 |
| Humectant | | | |
| Glycerin | 7.0 | 5.0 | 6.25 |
| Sorbitol | 5.0 | 5.0 | N/A |
| Sudsing Aid Anionic Surfactant | | | |
| Sodium Lauryl Sulphate | 2.0 | 1.75 | 1.25 |
| Tar Solubilizer and/or Flavor Solubilizer Nonionic Surfactant | | | |
| Cremophor RH40 | N/A | 0.85 | N/A |
| Cremophor RH60 | N/A | N/A | 0.50 |
| Polysorbate 20 | N/A | 1.5 | N/A |
| Polysorbate 80 | 0.75 | N/A | 0.75 |
| Cyclic Aromatic Essential Oil | | | |
| Methyl Salicylate | 2.0 | 2.25 | 0.50 |

TABLE 1-continued

| Ingredient | Example 1 | Example 2 | Example 3 |
| --- | --- | --- | --- |
| Flavor | | | |
| Essential Oil Preservative | 0.25 | 0.25 | 0.25 |
| Benzoic Acid | N/A | N/A | 0.10 |

All of the exemplified formulations represent satisfactory, pleasing, acceptable and effective deposit removing mouth rinses having satisfactory storage ability with respect to color, appearance, taste, and the like.

Generally, the preparation is prepared by adding the ingredients in the following sequence. First, a sudsing agent may be added to the vehicle. Next, the surfactants are added to the solvent. Then, any flavoring is added to the solvent/surfactant mixture. Finally, the vehicle and solvent solutions are mixed together.

To demonstrate the effectiveness of the present invention as compared to known oral rinses, an experiment was performed in which tobacco tar covered slides were exposed to an oral rinse prepared according to the present invention, and to two commercial products PLAX and LISTERINE. According the experiment, three identical samples of glass plates on which identical amounts of cigarette tar had been deposited or used. The samples were exposed to identical amounts of the three oral preparations.

The amounts of tar removed from the three samples and dissolved or dispersed within the solutions was determined by spectrophotometric analyses of each sample using a Bausch & Lomb spectronic 601 UV visible spectrophotometer. The analytical wavelength of the spectrophotometer was a 330 nm. Quartz cuvettes were used throughout these experiments.

After exposing the glass slides stained with the tar to the mouthwash, the absorbency of the spectrophotometer was set to 0 using a clean sample of the selected mouthwash product diluted at a ratio of 1 to 25 by volume with methanol. Samples of the oral preparations to which the tar stained glass slides were exposed were then diluted at a ratio of 1 to 25 by volume with methanol. The absorbencies of each of these solutions were then measured and recorded. Tar concentrations in each sample of the oral preparations were then determined from these data by reference to the absorbency obtained from a standard solution containing 0.250 milligrams per milliliter of cigarette tar in methanol, correcting for the 1 to 25 volume dilution of the experimental samples.

The results of the experiment, contained in Table 2 demonstrate that an oral preparation prepared according to the present invention removed more than ten times as much tobacco tar than either the PLAX or LISTERINE products. As can be seen from the table, the present invention removed at least 11 times the amount of tar from the samples as the commonly available products LISTERINE and PLAX. In fact, the other mouthwashes were not very effective at removing the tar. Additionally, the present invention accomplishes this large, unexpected increase in tar removal without using any abrading materials, as are commonly used in the prior art.

Observations of the results of the various solutions' effects on the tar also indicates the superiority of the present invention tar solubilizing ability. Immersing a tar stained slide in an embodiment of the present invention caused the solution to turn brown; this sample of the present invention was not hazy. The LISTERINE and PLAX containing samples became hazy. The haze in the solutions demonstrate that any suspended particles are large enough to scatter light. The present invention dissolved the tar into particles so small, they did not scatter light. This test is a standard indicator of solvent/solute solubility.

TABLE 2

| Sample | Tar Concentration mg/ml | Standard Deviation mg/ml |
| --- | --- | --- |
| PLAX | 0.229 | 0.006 |
| LISTERINE | 0.262 | 0.006 |
| Present Invention | 3.03 | 0.01 |

The present invention has also been tested on tobacco tar stained extracted teeth from humans. In these tests, the present invention was found to remove tobacco tar quickly, efficiently, and to a much greater degree than any known product.

Interim results of a human in-vivo clinical study shows a 45% tar stain reduction in the test population after one week of use. These studies also indicate that the present invention reduces the adhesive surfaces of bacteria within bacterial colonies. This effect possibly comes from the known ability of methyl salicylate to break down compounds having an adhesive character. By breaking down or at least partially reducing adhesive compounds on the bacteria, the present invention can reduce the ability of the bacteria to colonize. It is this ability to stick together that allows bacteria to colonize and eventually cause cavities.

An oral preparation according to the present invention will act to dissolve and/or disperse tar deposited on all surfaces within the mouth. In particular, the present invention will dissolve and/or disperse tar deposited on the gums, tongues, and other soft tissues within smokers' mouths. For example, cotton gauze saturated with a preparation prepared according to the present invention wiped on the tongues of smokers were colored brown from the removed tar. On the other hand, cotton gauze saturated with a water placebo were barely stained, and this staining was attributed to the physical action of the wiping on the tongue alone.

Additionally, the preparation of the present inventions is also suitable for use on denture material. In addition to being useful for dissolving tar, the present invention will also rapidly dissolve and/or disperse, remove from the mouth, and/or mask food, food odors, oils, and other hydrophobic materials, among other things. Examples include essential oils from onions and garlic, which the present invention has demonstrated the ability to remove from the mouth so that they cannot be detected.

I claim:

1. A toothpaste for smokers for solubilizing and removing cigarette tar deposits on the teeth, gums, tongue, other surfaces of the oral cavity, and dentures of smokers, comprising:

at least one nonionic surfactant in a concentration range of from about 0.3% to about 6.5% by weight;

methyl salicylate in a tobacco tar solubilizing concentration range of from about 0.06% to about 0.20% by weight;

at least one essential oil in a concentration range of from about 0.30% to about 2.0% by weight;

ethyl alcohol in a concentration range of from about 12.0% to about 20.0% by weight;

at least one anionic surfactant in a concentration range of from about 0.3% to about 4.5% by weight; and a gelling agent.

2. A toothpaste according to claim 1, further comprising at least one anionic surfactant in a concentration range of from about 0.3% to about 4.5% by weight and wherein said essential oil is a cyclic, preferably aromatic essential oil.

3. A toothpaste according to claim 1, wherein said anionic surfactant is selected from the group consisting of sodium lauryl sulfate and sodium ether lauryl sulfate.

4. A toothpaste according to claim 1, wherein said nonionic surfactant is selected from the group consisting of glycerol-polyethylene glycol oxystearate, polyoxyethylene esters or sorbitol laurate esters, polyoxyethylene sorbitan monolaurate, polyoxygthylene sorbitan monoisostearate, polyoxyethylene sorbitan monostearate, polyoxyethylene sorbitan monooleate, polyoxyethylene laurate esters, sorbitol laurate esters including polysorbates, and block polymers of polyoxyethylene and polyoxypropylene.

5. A toothpaste according to claim 1, wherein said cyclic aromatic essential oil includes at least one selected from the group consisting of methyl salicylate, anise, anethol, bergamot, camphor, cinnaminic anhydrides, clove, eucalyptol, peppermint, spearmint, and thyme.

6. A toothpaste according to claim 1, further comprising a solvent, a vehicle, at least one humectant, at least one flavoring, and at least one preservative.

7. A toothpaste according to claim 6, wherein said solvent is ethanol and is included in said oral preparation in a concentration range of from about 8.0% to about 30% by weight.

8. A toothpaste according to claim 6, wherein said vehicle is water and is included in said oral preparation in a concentration range of from about 50% to about 80% by weight.

9. A toothpaste according to claim 6, wherein said humectant includes at least one selected from the group consisting of glycerin and sorbitol and is included in said oral preparation in a concentration range of from about 3% to about 15% by weight.

10. A toothpaste according to claim 6, wherein said flavoring is at least one aromatic or cyclic essential oil and is included in said oral preparation in a concentration range of from about 0.1% to about 0.4% by weight.

11. A toothpaste according to claim 6, wherein said preservative includes at least one member selected from group consisting of benzoic acid and sodium benzoate and is included in said oral preparation in a concentration range of from about 0.1% to about 2.0% by weight.

12. A toothpaste according to claim 1, further comprising at least one sweetener in a concentration range up to about 0.7% by weight.

13. A toothpaste according to claim 1, further comprising at least one coloring agent in a concentration range up to about 0.5% by weight.

14. A method of solubilizing and removing cigarette tar deposits on the teeth, gums, tongue, other surfaces of the oral cavity, and dentures of smokers, comprising:

introducing into the mouth a toothpaste for dissolving or dispersing the tobacco tar deposits, said toothpaste comprising at least one nonionic surfactant in a concentration range of from about 0.3% to about 6.5% by weight; methyl salicylate in a tobacco tar solubilizing concentration range of from about 0.06% to about 0.20% by weight; at least one essential oil in a concentration range of from about 0.30% to about 2.0% by weight; ethyl alcohol in a concentration range of from about 12.0% to about 20.0% by weight; at least one anionic surfactant in a concentration range of from about 0.3% to about 4.5% by weight; and a gelling agent including at least one selected from the group consisting of silica aerogels, pyrogenic silica, silica precipitates, carboxymethyl cellulose, carboxyvinyl polymers, xanthan gum, and carrageenan.

15. A method according to claim 14, wherein said toothpaste further comprises at least one anionic surfactant in a concentration range of from about 0.3% to about 4.5% by weight and wherein said essential oil is a cyclic aromatic essential oil.

16. A method according to claim 15, wherein said anionic surfactant is selected from the group consisting of sodium lauryl sulfate and sodium ether lauryl sulfate.

17. A method according to claim 16, wherein said nonionic surfactant is selected from the group consisting of glycerol-polyethylene glycol oxystearate, polyoxyethylene esters or sorbitol laurate esters, polyoxyethylene sorbitan monolaurate, polyoxyethylene sorbitan monoisostearate, polyoxyethylene sorbitan monostearate, polyoxyethylene sorbitan monooleate, polyoxyethylene laurate esters, sorbitol laurate esters including polysorbates, and block polymers of polyoxyethylene and polyoxypropylene.

18. A method according to claim 14, wherein said cyclic aromatic essential oil is methyl salicylate.

19. A method according to claim 14, wherein said toothpaste further comprises a solvent, a vehicle, at least one humectant, at least one flavoring, and at least one preservative.

20. A method of solubilizing and removing tobacco tar deposits on the teeth, gums, tongue and other surfaces of the oral cavity, comprising contacting teeth or dentures of a smoker with a toothpaste for solubilizing, dissolving, or dispersing the tobacco tar deposits, said preparation comprising a mixture of:

at least one anionic surfactant in concentration range of from about 0.3% to about 4.5% by weight;

at least one nonionic surfactant in a concentration range of from about 0.3% to about 6.5% by weight;

methyl salicylate in a tobacco tar solubilizing concentration range of from about 0.06% to about 0.20% by weight;

ethyl alcohol in a concentration range of from about 12.0% to about 20.0% by weight; and at least one cyclic, preferably aromatic essential oil in a concentration range of from about 0.30% to about 2.0% by weight.

21. A toothpaste according to claim 1, wherein said gelling agent includes at least one member selected from the group consisting of silica aerogels, pyrogenic silica, silica precipitates, carboxymethyl cellulose, carboxyvinyl polymers, xanthan gum, and carrageenan.

* * * * *